US009687342B2

(12) United States Patent
Figulla et al.

(10) Patent No.: US 9,687,342 B2
(45) Date of Patent: Jun. 27, 2017

(54) VALVE PROSTHESIS FOR REPLACING AN ATRIOVENTRICULAR VALVE OF THE HEART WITH ANCHORING ELEMENT

(76) Inventors: Hans Reiner Figulla, Jena (DE); Alexander Lauten, Jena (DE)

(*) Notice: Subject to any disclaimer, the term of this patent is extended or adjusted under 35 U.S.C. 154(b) by 0 days.

(21) Appl. No.: 13/979,016

(22) PCT Filed: Jan. 11, 2011

(86) PCT No.: PCT/EP2011/000082
§ 371 (c)(1),
(2), (4) Date: Dec. 13, 2013

(87) PCT Pub. No.: WO2012/095116
PCT Pub. Date: Jul. 19, 2012

(65) Prior Publication Data
US 2014/0088695 A1    Mar. 27, 2014

(51) Int. Cl.
*A61F 2/24* (2006.01)
*A61F 2/848* (2013.01)

(52) U.S. Cl.
CPC .......... *A61F 2/2412* (2013.01); *A61F 2/2418* (2013.01); *A61F 2/2457* (2013.01); *A61F 2/848* (2013.01); *A61F 2220/0008* (2013.01); *A61F 2230/0065* (2013.01)

(58) Field of Classification Search
CPC ........ A61F 2/24; A61F 2/2409; A61F 2/2412; A61F 2/2418

USPC ....................................................... 623/1.14
See application file for complete search history.

(56) References Cited

U.S. PATENT DOCUMENTS

| 6,231,561 | B1* | 5/2001 | Frazier et al. ................. 604/500 |
| 8,449,599 | B2* | 5/2013 | Chau et al. ................... 623/1.26 |
| 2007/0050020 | A1 | 3/2007 | Spence |

FOREIGN PATENT DOCUMENTS

| WO | 03-037227 A2 | 5/2003 |
| WO | 2010-057262 A1 | 5/2010 |

OTHER PUBLICATIONS

State Intellectual Property Office, P.R. China, First Office Action mailed Feb. 28, 2015 with English translation in Chinese Patent Application No. 201180069211.5, 10 pages.

* cited by examiner

*Primary Examiner* — Katrina Stransky
*Assistant Examiner* — Wade P Schutte
(74) *Attorney, Agent, or Firm* — Inskeep IP Group, Inc.

(57) ABSTRACT

The invention relates to a valve prosthesis for replacing an atrioventricular valve of the heart, comprising an annular body, to which heart valve leaflets are attached and which can be inserted in the valve annulus of the heart, and further comprising at least one anchoring part, which protrudes from the annular body on the ventricle side and can be anchored in tissue.

12 Claims, 2 Drawing Sheets

Figure 1:
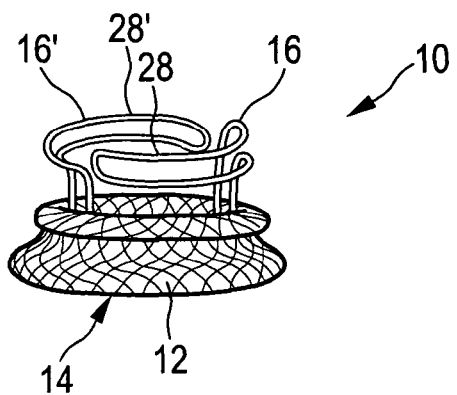

VALVE PROSTHESIS FOR REPLACING AN ATRIOVENTRICULAR VALVE OF THE HEART WITH ANCHORING ELEMENT

The invention relates to a valve prosthesis for replacing an Atrioventricular valve of the heart, i.e, the mitral valve or the tricuspid valve.

In patients with functional impairment of a heart valve, the use of open-heart surgery to insert a prosthetic valve (replacement valve) is often associated with increased risks due to the general condition of the patient. Consequently, heart valve prostheses are increasingly implanted in a minimally invasively manner via a catheter.

The prior art recognizes the use of highly compressible stents with replacement heart valve leaflets attached therein that are deliverable through a catheter for advancement to the site of the heart valve to be replaced and there releasable. For example, a balloon-expandable or self-expandable stent develops a radial expansion force in released state which force causes or at least promotes anchoring of the replacement valve prosthesis. A replacement aortic valve which can be anchored by a radial expansion force for such an anchoring of a valve prosthesis is particularly suitable at the place of a dysfunctional aortic valve. See, for example, EP 1994913 A2, EP 1469797 B1, EP 1259195 B1, WO 2007/051620 A1, WO 2007/048529 A1, EP 1980220 A1, WO 01/64137 A1, EP 1255510B3, and U.S. Pat. No. 5,411,552.

However, the mitral valve of the heart, which is the valve between the left atrium and the left ventricle, is not very suitable for a replacement prosthesis anchored mainly by a radial expansion force of a stent positively (by friction) anchored on the spot, since a widening of the annulus is to be avoided.

One objective of the present invention is to provide a valve prosthesis that allows replacement of an atrioventricular valve, which is implantable using a catheter, and allows for stable and orthotropic positioning and anchoring.

An inventive valve prosthesis for the replacement of an atrioventricular valve of the heart is provided that has
- an annular, i.e. ring shaped, body to which valve leaflets, which are known as valvular cusps, are attachable and which annular body is adapted to be inserted into a valve annulus of the heart, and
- at least one anchoring member that extends from the annular body in the direction of the ventricle and is adapted to be anchored to the chordae, the papillary muscles, or the cusps of the atrioventricular valve.

In accordance with the invention, the anchoring of the valve prosthesis is provided by means of hook-shaped anchoring elements that are fixedly connected with the annular body, in which or to which the valvular cusps (valve leaflets) are attached. The anchoring elements extend from the annular body in parallel to its axis into the ventricle, and they are dimensioned so that they can be hooked with a hook into tissue that is present at their vicinity, such as in particular chordae tendinae, papillary muscles or valvular cusps, which hook is provided at an end of the anchoring element that is oriented towards the ventricle. Hence, the two functions of the valve prosthesis, namely on the one hand to support and keep in place the replacement heart valve leaflets, and on the other hand the anchoring of the valve prosthesis, are kept spatially apart from each other: The annular body is positioned in the annulus and keeps there the replacement valvular cusps, while the anchoring elements in the afore described manner achieve the anchoring of the valve prosthesis by a distance from the annular body.

The annular body has preferably a diabolo shape, i.e. a waisted shape, so that the annulus can engage into a centrally oriented section of the annular body, which centrally oriented section has a reduced diameter in comparison to the ends of the annular body. The annular body is shaped with regard to its dimensions and its elastic properties, so that no radially oriented expansion forces that substantially expand the valve annulus are produced upon insertion into the valve annulus of the heart.

During systole, the ventricle is to be sealed off from the atrium. This sealing is provided by the replacement valve prosthesis. A force corresponding to the full blood pressure acts on the heart valve leaflets of the prosthesis. The valve prosthesis must be stably and durably orthotropically anchored to counter this force. The invention utilizes the insight that this force substantially acts in the direction of the central axis of the annular body (corresponding with the direction of the central axis of the annulus) so that the anchoring must absorb tensile forces in this direction.

Therefore, the inventive valve prosthesis provides necessary anchoring forces without generating friction between the prosthetic valve and the annulus. Rather, the valve prosthesis, during systole in which it assumes the closed state, is anchored by tensile supporting forces acting in the axial direction, that are introduced via the anchoring elements into the surrounding tissue, in particular the forces are introduced into the chordae where they are countered.

To this end, the anchoring elements are provided with hook shaped anchoring cub components, such that for example the anchoring element as a whole has the shape of an angular element that has an arm shaped component that substantially extends axially, which at its end which is oriented towards the atrium is fixed to the annular body, and in particular is rotationally fixed to the annular body, and at an end oriented towards the ventricle has a component that is bent around the axis of the annular body, and in such a manner can be hooked with tissue upon rotation of the anchoring elements, so that the valve prosthesis as a whole is securely anchored, in particular against the pressure from the ventricle.

For replacement of a mitral valve the invention includes preferably two diametrically opposed anchoring elements, while three anchoring elements are preferred for a tricuspid valve, which separate the circumference into sections of 120 degrees.

The annular body is preferably made from a wire mesh or braiding, in particular of a material with shape memory.

Heart valve leaflets, which may be used with the valve prosthesis of the invention and can be attached to or in the annular body, can be selected from the prior art as disclosed, for example, in U.S. Pat. No. 5,411,552 and EP 1,255,510 B3. For example, a valve leaflet obtained from a pig or a biological heart valve formed from a pericardium flap may be sewn into the annular body.

The invention provides a heart valve prosthesis with a ventricular-sided anchoring, which enables stable and orthotropic anchorage and positioning of the heart valve prosthesis. The anchoring prevents movement of the valve prosthesis in the axial direction. As used herein, axial direction, radial direction, and circumferential direction, refers to the annular body of said valve prosthesis or, in the implanted state, the annulus of the replaced Mitral or Tricuspid valve.

The inventive replacement atrioventricular valve may be balloon-expandable or self-expandable The replacement valve may be implanted by means of a catheter, transepitally, transapically via the apex of the heart, or retrograde through the aorta.

The positioning of the valve prosthesis with a catheter is preferably made in a procedure such that the anchoring elements as described are released from a first end of the catheter and are then anchored by their hooks in tissue, in particular by rotation of the entire valve prosthesis around the axis together with the anchoring elements, such that the annular body comes to rest with its longitudinal center approximately at the annulus of the valve to be replaced.

In a variant of the above described embodiments, the anchoring elements may be shaped so that their hook shaped anchoring sub components do not extend in circumferential direction, but rather include radially outwardly oriented hooks, which after release of the valve prosthesis are spread outwardly, such that an anchoring is enabled into the chordae or other tissue, such as leaflets (valve cusps) of the native atrioventricular valves.

The inventive anchoring elements are shaped to allow an unhindered flow of blood in the ventricle between them to provide access to the aorta and aortic valve.

In a further preferred embodiment of the invention, the axial length of the anchoring elements is adjustable, e.g. via a lockable telescopic arrangement, a threaded connection, or the like, so that the surgeon may adjust locally to the anatomical circumstances.

Chorae or tendons in the present context include also connecting segments of these chordae or tendons close to the cusps of the valve.

Figure 2:
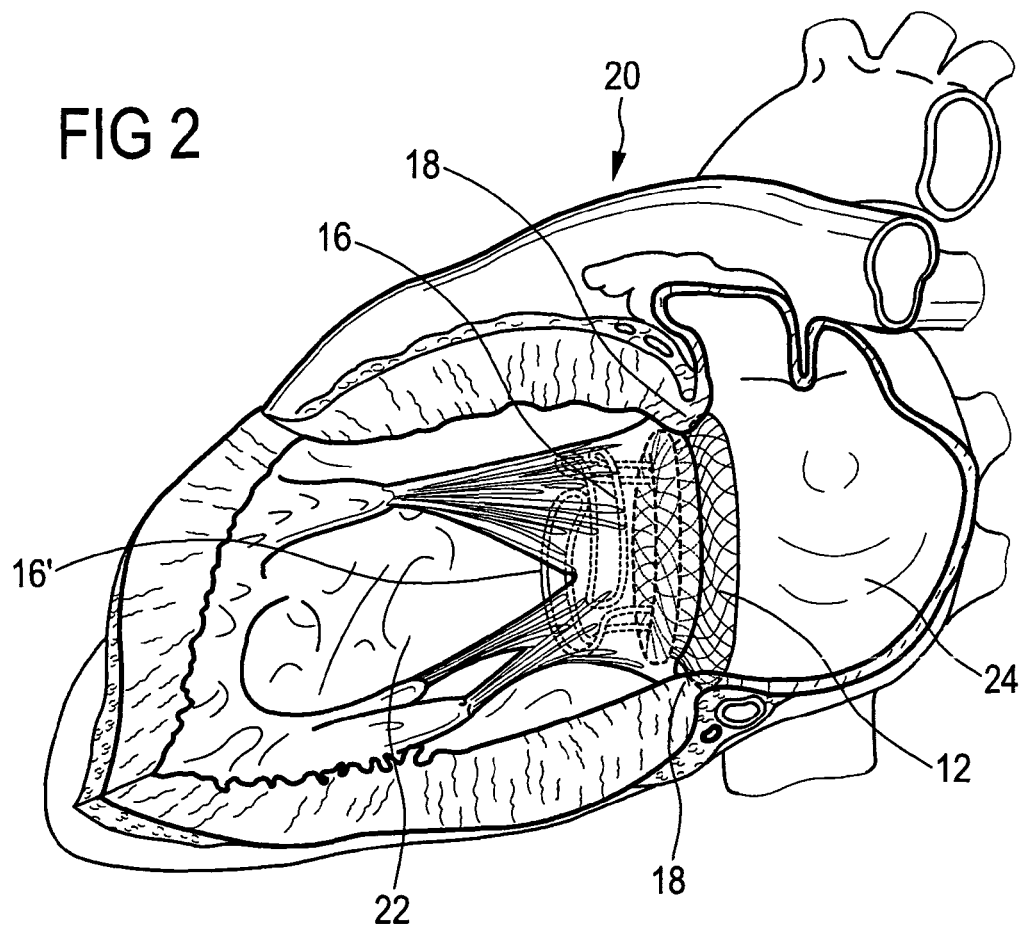
Figure 3:
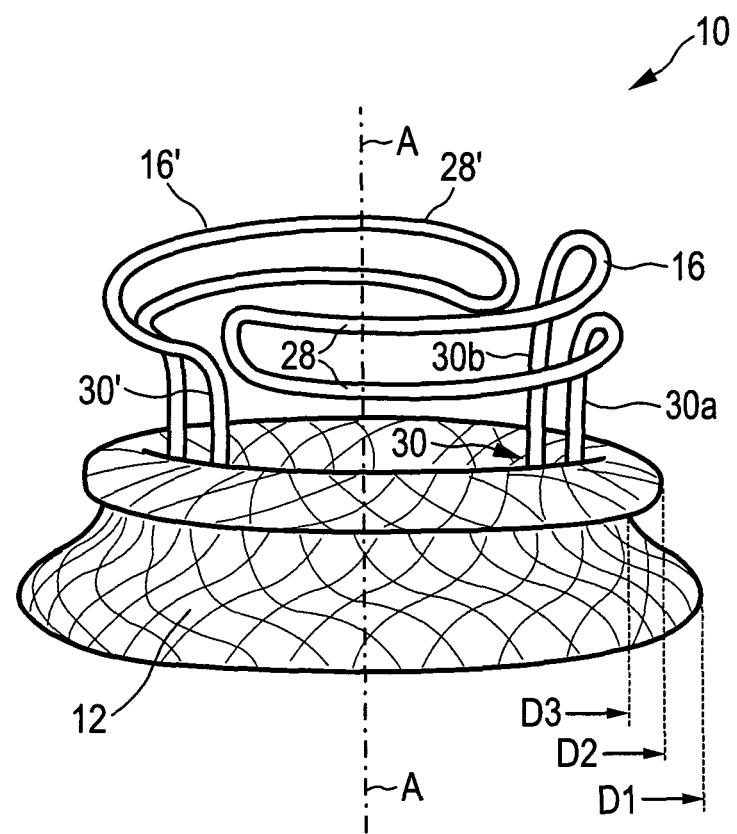

Embodiments of the invention will be elucidated with reference to the drawings, which show:

FIG. 1—a schematic valve prosthesis to replace an atrioventricular valve of the heart;

FIG. 2—a valve prosthesis according to FIG. 1 in the implanted state in the heart, and FIG. 3—a valve prosthesis on an enlarged scale.

The valve prosthesis 10 for replacement of an atrioventricular valve of the heart illustrated in FIG. 1 has an annular body 12 in which heart valve leaflets, not shown in detail, are fixed. Known systems for heart valve flaps 14 may be used, for example leaflets from pericardium, or obtained from porcine heart valves, which are sewn into the annular body 12. The annular body 12 is formed from a wire mesh or braiding and the elastic characteristics of the wire and the dimensions of the annular body 12 are selected so that the annular body, in use of the valve prosthesis as a mitral valve or tricuspid valve, and in contrast to a typical stent, does not produce a radial expansion force that substantially expands the native valve annulus.

For the wire mesh of the annular body 12, a metal shape-memory can be used, for example, Nitinol.

As FIGS. 1, 2 and 3 illustrate, the annular body is rotationally symmetrical about the axis A. The atrial side diameter D1 of the annular body 12 is greater than the diameter D2 of the ventricular side and this, in turn, is greater than a central diameter D3 of the annular body 12.

As the figures illustrate, the ventricular-side anchor members 16, 16' protrude from the annular body 12 in the axial direction. As FIG. 2 illustrates, these anchor members 16, 16' protrude into the ventricle 22. The annular body 12 is positioned with its central portion, that is the portion of reduced diameter D3, in the annulus of the mitral valve 18. FIG. 2 thus illustrates the use of the valve prosthesis between the left atrium and left ventricle. The area of the annular body 12 having an enlarged diameter D1 abuts the atrial side of the annulus 18 and the fixes valve prosthesis in its open state when blood flows from the atrium 24 into the ventricle 22.

The anchoring elements 16, 16' are in the embodiment, two components respectively, namely on the one hand, first arms 30a, 30b which extend substantially parallel to the axis A of the annular body 12 and transition at their ends on the ventricular side of the annular body into loop-shaped bends that form components 28, 28' which bend like a hook around the axis A of the annular body 12 in circumferential direction of the annular body, such as is illustrated in detail in FIG. 3.

In the illustrated embodiment, an arm 30 has two arm components 30a, 30b for the rotationally fixed connection between anchoring part 16 and annular body 12, wherein the two arm components 30a, 30b extend substantially parallel to the axis A of the annular body and on their ends at the ventricular side transition to loop-type bend components 28, 28' of the anchoring elements that extend circumferentially. The anchor members 16, 16' are formed of a suitable metal wire.

The anchor members 16 are, according to a given anatomical situation, dimensioned such that the distance from the annulus 18 to the ventricle-facing end of the anchoring element is in the range of from 5 to 40 mm, preferably in the range of 5 to 20 mm or in the range of 10 to 25 mm.

Similar to a stent-valve prosthesis, the described valve prosthesis is highly compressible and can be positioned via a minimally invasive catheter in the heart, namely in particular transepitally, transapically via the apex of the heart, or even retrograde via the aorta. Catheter techniques known by those of skill in the art can be used for this purpose.

The procedure for insertion of the described valve prosthesis includes that the anchoring elements 16,16' first be released from the catheter at the area of the valve being replaced. The anchoring of the embodiment illustrated in FIGS. 1-3 by anchoring members 16' is accomplished by rotation of the annular member 12 with the anchoring elements 16, 16' rotationally fixedly attached thereto, which with its components 28, 28' for example hook in the chordae or also the native semilunar valve. The rotation can be accomplished by rotation of the catheter itself or by a pusher in the catheter, which allows a rotary engagement with the annular body 12. After this engagement and anchoring of the anchoring elements in the tissue, such as the chordae tendinae of the native or semilunar valve then occurs, the full release of the valve prosthesis from the catheter, wherein the diabolo-shaped annular body with its longitudinally central portion of reduced diameter is fixed in the annulus 18, as illustrated in FIG. 2.

In a modification of the embodiment described above, the anchoring components 28, 28' can be modified so that they do not extend in the circumferential direction, but radially outward so that they can be moved by spreading after release into anchoring engagement with the chordae or in anchoring engagement with native leaflets, according to the anatomical conditions.

The invention claimed is:

1. A valve prosthesis for replacing an atrioventricular valve of a heart, the prosthesis comprising:
  a ring-shaped body, to which valvular cusps are attached wherein the ring-shaped body is adapted to be inserted into a valve annulus of the heart, and
  at least one anchoring element that is non-rotatably affixed to the ring-shaped body and that is configured to protrude in the direction of the ventricle which is a direction pointing away from an atrial side of the ring-shaped body, wherein the at least one anchoring element is adapted to be anchored in chordae, papillary muscles or cusps of the atrioventricular valve upon rotation of said ring-shaped body in a direction of rotation around an axis thereof wherein:

the at least one anchoring element comprises an axial component that extends an axial distance from said ring-shaped body and is configured to extend in the direction of the ventricle and a curved component extending circumferentially and being bent around the axis of the ring-shaped body from the axial component such that the curved component is configured to engage with valve chordae upon said rotation, and wherein, in the closed state of the valve, the at least one anchoring element is adapted to transfer essentially axial forces into chordae of the heart.

2. The valve prosthesis according to claim 1, comprising one, two or three anchoring elements.

3. The valve prosthesis according to claim 1, wherein the ring-shaped body, at its atrial side, has a diameter that is larger than a diameter of an intermediate region of the ring-shaped body.

4. The valve prosthesis according to claim 1, wherein the ring-shaped body, at its ventricular side, has a diameter that is larger than a diameter of an intermediate region of the ring-shaped body.

5. The valve prosthesis according to claim 3, wherein the diameter at the atrial side is larger than the diameter at the ventricular side.

6. The valve prosthesis according to claim 1, wherein the ring-shaped body does not radially expand the valve annulus when implanted in the annulus of the heart.

7. The valve prosthesis according to claim 1, wherein said prosthesis is a replacement valve for a mitral valve and said prosthesis has two anchoring elements.

8. The valve prosthesis according to claim 1, wherein said prosthesis is a replacement valve for a tricuspid valve and said prosthesis has three anchoring elements.

9. The valve prosthesis according to claim 1, wherein the ring-shaped body is formed from a meshwork made from a material having shape memory.

10. The valve prosthesis according to claim 1, wherein the ring-shaped body is balloon-expandable.

11. The valve prosthesis according to claim 1, wherein the ring-shaped body is self-expandable.

12. The valve prosthesis according to claim 1, wherein a length of an anchoring element is adjustable in an axial direction.

* * * * *